(12) United States Patent
Agarwal et al.

(10) Patent No.: US 9,323,928 B2
(45) Date of Patent: Apr. 26, 2016

(54) SYSTEM AND METHOD FOR NON-SIGNATURE BASED DETECTION OF MALICIOUS PROCESSES

(75) Inventors: Romanch Agarwal, Lucknow (IN); Prabhat Kumar Singh, Bangalore (IN); Nitin Jyoti, Bangalore (IN); Harinath Ramachetty Vishwanath, Bangalore (IN); Palasamudram Ramagopal Prashanth, Bangalore (IN)

(73) Assignee: McAfee, Inc., Santa Clara, CA (US)

( * ) Notice: Subject to any disclaimer, the term of this patent is extended or adjusted under 35 U.S.C. 154(b) by 189 days.

(21) Appl. No.: 13/151,173

(22) Filed: Jun. 1, 2011

(65) Prior Publication Data

US 2012/0311708 A1   Dec. 6, 2012

(51) Int. Cl.
| | |
|---|---|
| G06F 21/00 | (2013.01) |
| G06F 21/56 | (2013.01) |
| G06F 21/55 | (2013.01) |
| G06F 17/30 | (2006.01) |
| G06F 19/24 | (2011.01) |
| H04L 29/06 | (2006.01) |

(52) U.S. Cl.
CPC ............... *G06F 21/56* (2013.01); *G06F 21/55* (2013.01); *G06F 21/566* (2013.01); *G06F 17/3053* (2013.01); *G06F 17/30598* (2013.01); *G06F 19/24* (2013.01); *H04L 63/145* (2013.01)

(58) Field of Classification Search
CPC ....... G06F 21/56; G06F 21/566; G06F 19/24; G06F 17/3053; G06F 17/30598; G06F 21/55; G06F 21/556; H04L 63/102; H04L 63/145
USPC ................................................ 726/22–24
See application file for complete search history.

(56) References Cited

U.S. PATENT DOCUMENTS

| | | | | |
|---|---|---|---|---|
| 7,624,444 | B2 * | 11/2009 | Gupta et al. ..................... | 726/23 |
| 2004/0054917 | A1 | 3/2004 | Obrecht et al. | |
| 2004/0064736 | A1 | 4/2004 | Obrecht et al. ............... | 713/201 |
| 2005/0283837 | A1 | 12/2005 | Olivier et al. | |
| 2008/0016339 | A1 | 1/2008 | Shukla | |
| 2008/0127336 | A1 * | 5/2008 | Sun et al. ........................ | 726/22 |
| 2008/0263659 | A1 * | 10/2008 | Alme .............................. | 726/22 |
| 2009/0013405 | A1 * | 1/2009 | Schipka ......................... | 726/22 |
| 2009/0307771 | A1 * | 12/2009 | Rajan et al. .................... | 726/22 |

(Continued)

FOREIGN PATENT DOCUMENTS

| | | |
|---|---|---|
| CN | 103782303 A | 5/2014 |
| JP | 2008-021274 A | 1/2008 |

(Continued)

OTHER PUBLICATIONS

International Search Report and Written Opinion; PCT/US2012/040428; pp. 11, Dec. 20, 2012.

(Continued)

*Primary Examiner* — Carl Colin
*Assistant Examiner* — Gary Lavelle
(74) *Attorney, Agent, or Firm* — Baker Botts L.L.P.

(57) ABSTRACT

Systems and methods for detecting malicious processes in a non-signature based manner are disclosed. The system and method may include gathering features of processes running on an electronic device, applying a set of rules to the features, and applying a statistical analysis to the results of the rules application to determine whether a process should be classified into one or more of a plurality of process categories.

31 Claims, 2 Drawing Sheets

(56) References Cited

U.S. PATENT DOCUMENTS

| | | | |
|---|---|---|---|
| 2010/0153316 A1* | 6/2010 | Duffield et al. | 706/12 |
| 2010/0180344 A1 | 7/2010 | Malyshev et al. | 726/23 |
| 2010/0313270 A1* | 12/2010 | Kim et al. | 726/24 |
| 2011/0167474 A1* | 7/2011 | Sinha et al. | 726/1 |
| 2012/0159620 A1* | 6/2012 | Seifert et al. | 726/22 |
| 2012/0167218 A1* | 6/2012 | Poornachandran et al. | 726/24 |
| 2012/0210423 A1* | 8/2012 | Friedrichs et al. | 726/22 |

FOREIGN PATENT DOCUMENTS

| | | |
|---|---|---|
| JP | 2008-129707 A | 6/2008 |
| JP | 2012-083909 A | 4/2012 |
| WO | 2012167056 A2 | 12/2012 |
| WO | 2012167056 A3 | 2/2013 |

OTHER PUBLICATIONS

Preliminary Report on Patentability; PCT/US2012/040428; pp. 8, Dec. 12, 2013.

Office Action received for Japanese Patent Application No. 2014-513736, mailed on Nov. 4, 2014, 3 pages of English Translation and 3 pages of Japanese Office Action.

Extended European Search Report; Appl. No. 12793684.7-1870; 8 pages, Feb. 5, 2015.

* cited by examiner

SYSTEM AND METHOD FOR NON-SIGNATURE BASED DETECTION OF MALICIOUS PROCESSES

TECHNICAL FIELD

The present disclosure relates in general to information security, and more particularly to detecting malware in a non-signature based manner.

BACKGROUND

As the ubiquity and importance of digitally stored data continues to rise, the importance of keeping that data secure rises accordingly. While companies and individuals seek to protect their data, other individuals, organizations, and corporations seek to exploit security holes in order to access that data and/or wreak havoc on the computer systems themselves. Generally the different types of software that seek to exploit security holes can be termed "malware," and may be categorized into groups including viruses, worms, adware, spyware, and others.

Many different products have attempted to protect computer systems and their associated data from attack by malware. One such approach is the use of anti-malware programs such as McAfee AntiVirus, McAfee Internet Security, and McAfee Total Protection. Some anti-malware programs rely on the use of malware signatures for detection. These signatures may be based on the identity of previously identified malware or on some hash of the malware file or other structural identifier. Another approach for identifying malware is based on the behavior of a file. For example, anti-malware software may monitor an electronic device for processes attempting to access restricted portions of memory.

These approaches, however, rely on static signatures and/or a large amount of processing power to track process behavior. Additionally, signature databases can become exceedingly large as more and more malware is identified. Further, small changes to malware files may defeat attempts to lower the size of signature databases as the hash of a slightly modified malware file may be different from the original hash. Hardware issues may also arise as a consistent network connection may be required to ensure the most recent versions of malware signatures are available. Finally, reliance on signatures can make a system vulnerable to zero day attacks—attacks by previously unidentified malware.

SUMMARY OF THE DISCLOSURE

In accordance with the teachings of the present disclosure, the disadvantages and problems associated with detecting a denial of service attack on an electronic device may be improved, reduced, or eliminated.

In accordance with one embodiment of the present disclosure, a method for classifying a plurality of processes into a plurality of process categories is described. The method may include collecting a plurality of features of the process, applying a plurality of classification rules to the plurality of features to produce a plurality of weighted threat scores, wherein each of the plurality of classification rules corresponds to a one or more of the plurality of process categories, comparing the plurality of weighted threat scores to a plurality of threshold values, wherein each of the plurality of threshold values corresponds to one of the plurality of process categories, and classifying the process in the one or more process categories based at least on the comparison of the plurality of weighted threat scores to the plurality of predetermined thresholds.

In accordance with another embodiment of the present disclosure, a system for classifying a plurality of processes into a plurality of process categories is described. The system may include a processor configured to collect a plurality of features of the process, apply a plurality of classification rules to the plurality of features to produce a plurality of weighted threat scores, wherein each of the plurality of classification rules corresponds to a one or more of the plurality of process categories, compare the plurality of weighted threat scores to a plurality of threshold values, wherein each of the plurality of threshold values corresponds to one of the plurality of process categories, and classify the process in the one or more process categories based at least on the comparison of the plurality of weighted threat scores to the plurality of predetermined thresholds.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION

Figure 1:
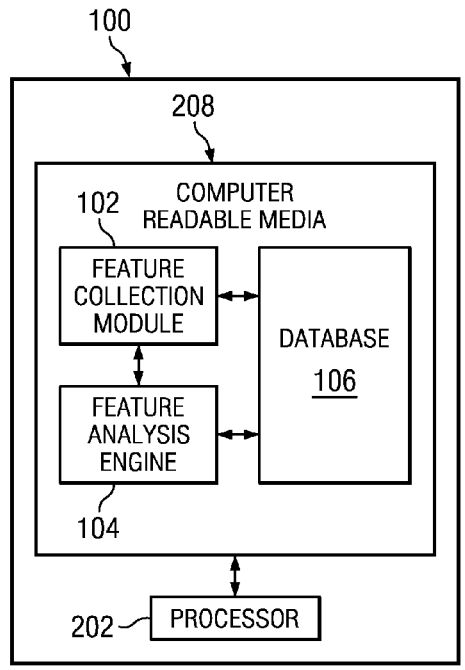
FIG. 1 illustrates a high level diagram of an electronic device for detecting malicious processes running on electronic device, in accordance with certain embodiments of the present disclosure.
Figure 3:
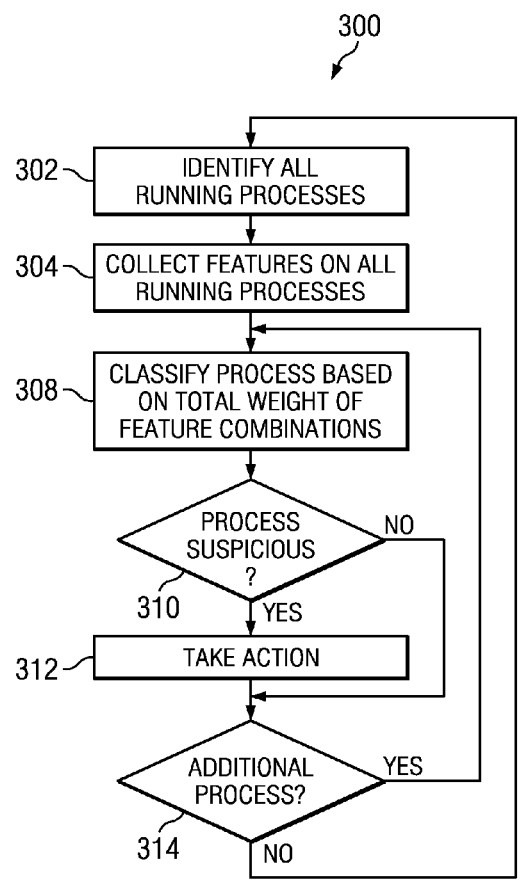
FIG. 3 illustrates a flow chart of an example method for detecting malicious processes running on electronic device, in accordance with certain embodiments of the present disclosure.
Figure 2:
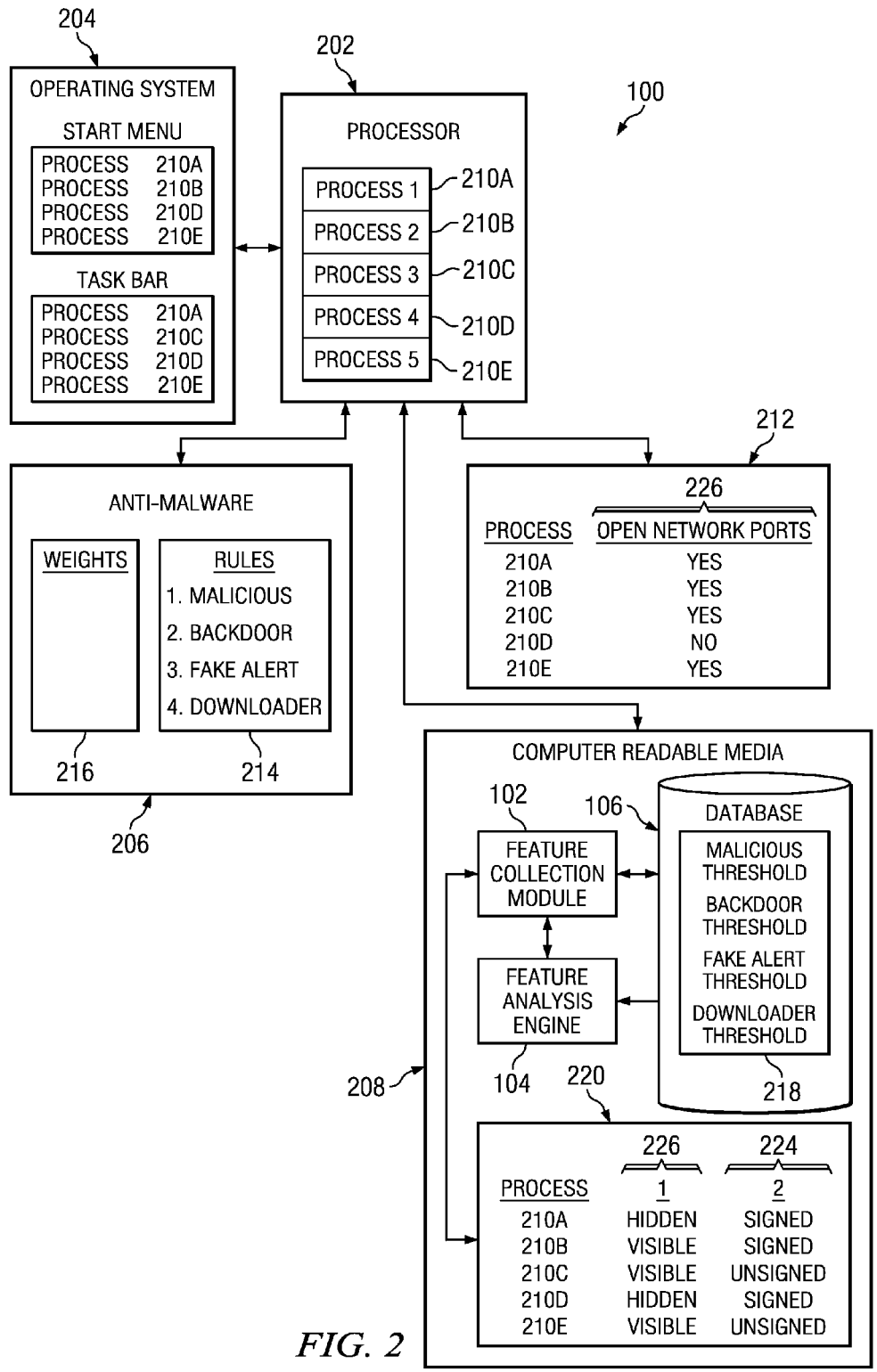
FIG. 2 illustrates an alternative high level diagram of electronic device for detecting malicious processes running on electronic device, in accordance with certain embodiments of the present disclosure.

Preferred embodiments and their advantages are best understood by reference to FIGS. 1 through 3, wherein like numbers are used to indicate like and corresponding parts.

For the purposes of this disclosure, an electronic device system may include any device, subdevice, or combination of devices and/or subdevices capable of storing, processing, sending, receiving, using, or handling data stored in digital form, including data stored on computer readable media. Computer readable media may include any device, subdevice, or combination of devices and/or subdevices configured to store digital data, including without limitation hard disk drives, flash memory, read only memory, random access memory, optical memory, solid state memory, or any other type of removable and/or fixed media used to store digital data.

FIG. 1 illustrates a high level diagram of an electronic device 100 for detecting malicious processes running on electronic device 100, in accordance with certain embodiments of the present disclosure. Electronic device 100 may be configured to run a number of processes. Generally, a process may be an instance of a computer program currently executing on electronic device 100. Electronic device may run any number of processes concurrently. As an illustrative example, a process may be the currently executing portion of a word processing program, web browser, operating system processes such as a print spooler or task manager, a network activity monitor, or any other instance of a computer program currently executing on electronic device 100. In some embodiments, these processes may be classifiable into one or more process categories. These categories may include benign processes and malicious processes. Benign processes may be those processes running on electronic device 100 with the knowledge and/or authority of the user or system operator. A malicious process may be a process running on electronic device 100 without the knowledge and/or authority of the user or system operator, or may be a process that has some behavior harmful to electronic device 100 or to the user or operator of electronic device 100. In some configurations, these malicious processes may be referred to generally as "malware."

Electronic device 100 may be any type of electronic device, including a laptop computer, desktop computer, and/or cellular telephone. In some embodiments, electronic device 100 may also be a server, cluster of servers, virtual machine, or other computing hardware, firmware, and/or software configured to run on hardware and/or firmware.

In some embodiments, electronic device 100 may include processor 202 and computer readable media 208. Processor 202 may be any appropriate microprocessor configured to execute instructions for electronic device. As illustrative examples, processor 202 may be a personal computer processor (e.g., Intel Core 2 Duo, Intel Core i3, or AMD Turion processor), or cellular telephone processor (e.g., Samsung S5PC110), or any other appropriate microprocessor.

Processor 202 may be communicatively coupled to computer readable media 208. Computer readable media 208 may include any appropriate computer readable media, including hard disk drives, RAM, ROM, optical media, network storage devices, distributed storage device, clustered storage device, virtual disk, or any other appropriate computer readable media.

In some embodiments, electronic device 100 may include one or more modules implemented as hardware components or stored on computer readable media 208 and executable by processor 202, including feature collection module 102, feature analysis engine 104, and database 106. In the illustrated embodiment of FIG. 1, feature collection module 102, feature analysis engine 104, and database 106 are depicted as stored in computer readable media 208. However, in some embodiments, the modules may be stored on the same or different computer readable media 208, on the same or different electronic devices 100, or implemented in hardware, firmware, or some combination thereof.

In some embodiments, feature collection module 102 may be configured to collect features about processes running on electronic device 100. As an illustrative example, a feature of a process may be whether or not it is associated with the Start Menu in a Windows operating system. Feature analysis engine 104 may be generally configured to analyze the features collected by feature collection module 102 in order to determine whether or not the process under analysis is malicious or benign, and/or to further classify the process into one or more subcategories of malicious processes.

Although feature collection module 102, feature analysis engine 104, and database 106 are illustrated as being resident within the same electronic device 100, in some embodiments, they may be present in the same or different electronic device(s) 100. For example, database 106 may be present on a central server, while feature collection module 102 and feature analysis engine 104 may be present on a local client machine. As another example, database 106 may be present in a hypervisor resident on an electronic device, where database 106 may service multiple feature collection modules 102 and multiple features analysis engines 104 that may be present in multiple guest operating systems communicatively coupled to the hypervisor. As yet another example, feature collection module 102, features analysis engine 104, and database 106 may be part of an integrated software program executable on computer readable media, or may be separate software programs and/or separate components, functions, or routines of a larger software program executable on computer readable media.

In some embodiments, feature collection module 102 may be generally operable to collect a plurality of features of a set of processes running on electronic device 100 in order to classify the processes as malicious or benign, as described in more detail below with reference to FIGS. 2-3. Generally, a process feature is an attribute describing a behavior, status, file size, file type, or other attribute of a process executing on electronic device 100. For example, features may include whether a process is associated with a start menu of an operating system of electronic device 100, associated with a task bar of the operating system, hidden or invisible, signed or unsigned, and/or requesting open network ports.

Feature analysis engine 104 may be generally operable to analyze the collected features. In some embodiments, this may include applying a plurality of classification rules 214 to the collected features. These rules 214 may include assigning weights to the collected features, performing a statistical analysis of the weighted totals, and producing a weighted threat score for each process, as described in more detail below with reference to FIGS. 2-3. In some embodiments, feature analysis engine 104 may be further operable to compare the weighted threat scores to a set of predetermined thresholds stored in database 106 in order to classify the process as either malicious or benign. In the same or different embodiments, feature analysis engine 104 may be further operable to classify the process into one or more malware families based at least on the weighted threat score(s), as described in more detail below with reference to FIGS. 2-3.

In operation, electronic device 100 may be generally configured to classify a plurality of processes into one or more process categories. A process may be an instance of a computer program currently executing on electronic device 100. Electronic device may run any number of processes concurrently. As an illustrative example, a process may be the currently executing a portion of a word processing program, web browser, operating system processes such as a print spooler or task manager, a network activity monitor, or any other instance of a computer program currently executing on electronic device 100. In some embodiments, these processes may be classifiable into one or more process categories. These categories may include benign processes and malicious processes. Benign processes may be those processes running on electronic device 100 with the knowledge and/or authority of the user or system operator. A malicious process may be a process running on electronic device 100 without the knowledge and/or authority of the user or system operator, or may be a process that has some behavior harmful to electronic device 100 or to the user or operator of electronic device 100. In some configurations, these malicious processes may be referred to generally as "malware."

In the same or other embodiments, malicious processes may be further classified into subcategories. As described in more detail below with reference to FIGS. 2-3. These subcategories may include certain types of malware such as backdoor processes, fake alert processes, and downloader processes. More, fewer, or other categories of malicious processes may be implemented in a given configuration without departing from the scope of the present disclosure.

As described in more detail below with reference to FIGS. 2-3, electronic device 100 may be generally configured to classify processes into one or more process categories by creating a set of rules 214 useful in said classification, collecting features from each process running on electronic device 100, applying the set of rules 214 to the collected features, appropriately weighting the results of that application, and comparing the weighted results to a set of threshold values.

In some embodiments, electronic device 100 may be generally configured to collect features from the processes running on electronic device 100 by gathering data about those processes from various hardware, firmware, software, or some combination of hardware, firmware, and/or software either part of, or communicatively coupled to, electronic device 100.

FIG. 2 illustrates the electronic device 100 of FIG. 1 in more detail, in accordance with certain embodiments of the present disclosure. In some embodiments, electronic device 100 may include processor 202 communicatively coupled to operating system 204, anti-malware component 206, computer readable media 208, and network interface 212. As described in more detail above with reference to FIG. 1 and below with reference to FIG. 3, electronic device 100 may include computer readable media 208 storing feature collection module 102, feature analysis engine 104, and database 106, all communicatively coupled to one another. Computer readable media 208 may also include process information module 220 communicatively coupled to feature collection module 102. In the same or alternative embodiments, electronic device 100 may include processor 202 configured to execute the instructions provided by feature collection module 102, feature analysis engine 104, and/or database 106.

In some embodiments, processor 202 may be configured to run a number of processes 210. Generally, a process 210 may be an instance of a computer program currently executing on electronic device 100. Electronic device may run any number of processes 210 concurrently. As an illustrative example, processor 202 is shown running five processes 210, labeled as processes 210 A, 210 B, 210 C, 210 D, and 210 E for ease of description. Although five processes 210 are depicted, more, fewer, or different processes could be present in a given configuration without departing from the scope of the present disclosure.

Processor 202 may be configured to retrieve data from operating system 204, anti-malware component 206, computer readable media 208, and/or network interface 212. In some embodiments, operating system 204 may be any operating system executing on processor 202 or another processor 202 of electronic device 100 or another electronic device 100. As an illustrative example, operating system 204 may be an actual or virtual instance of Windows XP, Windows 7, Linux, UNIX, Mac OS, or any other operating system configured to run on electronic device 100. Operating system 204 may be configured to have certain programs, routines, or subroutines running on operating system 204 that may provide information valuable to the classification of a process 210 as malicious or benign. For example, operating system 204 may include a "start menu" configured to provide an end user easy access to some applications. Some processes 210 running on electronic device 100 may be associated with the start menu, while others may not. In the illustrated example of FIG. 2, Processes 210 A, 210 B, 210 D, 210 E are associated with the start menu. For example, process 210 may be the currently executing instance of a word processing application such as Microsoft Word. In some configurations, the application may have an associated shortcut included in the start menu. Information regarding a process's association with the start menu may be helpful in classifying the process as malicious or benign, as the application associated with a malicious process may be less likely to be included in the start menu.

Additionally, operating system 204 may include a "task bar" configured to provide the status of certain processes 210 running on electronic device 100. In the illustrated example of FIG. 2, processes 210 A, 210 C, 210 D, 10E are associated with the task bar. For example, process 210 may be the currently executing instance of a network status application such as that used by a Windows operating system. Information regarding a process's association with the task bar may be helpful in classifying the process as malicious or benign, as certain types of malicious processes attempt to take advantage of the task bar to encourage an end user to engage the malicious process. However, many types of benign programs, such as the network status application, make use of the status bar as well. As described in more detail below with reference to FIG. 3, it is often more helpful to consider features of processes together than to consider certain types of behavior alone.

Although the illustrative examples of "start menu" and "task bar" are depicted as routines running within operating system 204, more, fewer, or different routines may be running and/or analyzed within operating system 204, as described in more detail below with reference to FIG. 3.

In some embodiments, electronic device 100 may also include anti-malware component 206 communicatively coupled to processor 202. Anti-malware component may be any hardware, firmware, software stored on computer readable media and executable by hardware and/or firmware, or any combination thereof. In some embodiments, anti-malware component 206 may be an application running within operating system 204. In other embodiments, anti-malware component 206 may be an application running outside of operating system 204, for example in a pre-boot environment. In still further embodiments, anti-malware component 206 may comprise multiple subcomponents, with some subcomponents running inside operating system 204 and some subcomponents running outside operating system 204. As an illustrative example, anti-malware component 206 may include some or all of the following: an agent running inside operating system 204 and an analysis engine running outside operating system 204.

In some embodiments, anti-malware component 206 may be configured to store a plurality of rules 214. Rules 214 may include a set of rules 214 for each category of processes 210. For example, malicious processes, backdoor processes, fake alert processes, downloader processes, and benign processes may each have their own sets of rules. In some embodiments, these families of rules may describe certain features and collections of features to be tested in order to classify process 210 into one or more categories. In some embodiments, feature analysis engine 104 may be configured to apply rules 214 to collected features in an effort to classify those processes 210 as malicious or benign. In other embodiments, some or all of the functionality of feature analysis engine may be performed by anti-malware component 206. For example, in a configuration in which anti-malware component 206 is stored entirely on computer readable media 208, anti-malware component 206 may be configured to store rules 214, as well as apply them to processes 210.

The results of applying these rules 214 may, in some embodiments, be weighted and compared against a set of predetermined threshold values 218. In some embodiments, the weights 216 to be applied to rules 214 may be stored by anti-malware component 206 and applied by feature analysis engine 104. In the same or other embodiments, weights 216 may be stored in database 106 of computer readable media 208. In still other embodiments, weights 216 may be applied to rules 214 by anti-malware component 206.

As described in more detail below with reference to FIG. 3, each rule 214 of each category of processes may have a weight 216 assigned to it. After weighting the results of the rules' applications, a statistical analysis may be performed by feature analysis engine 104 to determine a total weighted threat score, as described in more detail below with reference to FIG. 3. For example, "backdoor" processes may have a set of rules used to classify processes 210 into that category. Each rule 214 associated with this set of rules may have an associated weight 216. As an example statistical analysis, feature analysis engine 104 may add together the weighted results of applying the set of rules to a process 210 to determine whether that process 210 should be classified as a backdoor process. In other embodiments, anti-malware component 206 may perform the statistical analysis.

After weighting the results of the rules' application, the weighted results may be compared against a set of threshold values 218 by feature analysis engine 104. These threshold values 218 may each correspond to a particular category of process 210. As an illustrative example, these thresholds 218 may include a malicious process threshold, a "backdoor" malware threshold, a "fake alert" malware threshold, and/or a "downloader" malware threshold. These and other illustrative examples are described in more detail below with reference to FIG. 3. In other embodiments, anti-malware component 206 may compare the weighted results against the set of threshold values 218.

Electronic device 100 may also include computer readable media 208. Computer readable media 208 may include any appropriate computer readable media, including hard disk drives, RAM, ROM, optical media, network storage devices, distributed storage device, clustered storage device, virtual disk, or any other appropriate computer readable media. Electronic device 100 may include one or more instances of computer readable media 208. In some embodiments, computer readable media 208 may include feature collection module 102, feature analysis engine 104, and database 106, as described in more detail above with reference to FIG. 2.

In some embodiments, computer readable media 208 may also include process information module 220. Process information module 220 may include data representative of certain features of processes 210 running on electronic device 100. In the illustrated example of FIG. 2, process information module 220 includes data representative of two features of processes 210. The first illustrative feature is hidden feature 222. Hidden feature 222 may indicate whether process 210 is hidden to the end user and/or to operating system 204. The second illustrative feature is signed feature 224. Signed feature 224 may indicate whether process 210 is signed or unsigned by the make and/or distributor of process 210. For example, process 210A may be hidden and signed, process 210B may be visible and signed, process 210C may be visible and unsigned, etc. Although five processes 210 are shown as associated with computer readable media 208, more, fewer, or different processes 210 may be running at any given time. In some embodiments, only a subset of active processes 210 may be being analyzed, and therefore information regarding only that subset may be collected. As described in more detail below with reference to FIG. 3, the attribute values associated with each of the processes 210 under analysis may be used to classify each process 210 as malicious or benign and/or to classify the process 210 into one or more categories of malicious processes.

In some embodiments, electronic device 100 may include network interface 212 communicatively coupled to processor 202. Network interface 212 may be any hardware, firmware, software stored on computer readable media and executable by hardware and/or firmware, or any combination thereof. In some embodiments, network interface 212 may be an application associated with a Network Interface Card ("NIC") and configured to monitor some or all data associated with said NIC. In other embodiments, network interface 212 may be some portion of hardware and/or firmware associated with a NIC and configured to communicate some or all data associated with said NIC. In still further embodiments, network interface 212 may comprise multiple subcomponents, with some subcomponents running inside operating system 204 as software stored on computer readable media and executable by hardware and/or firmware, some subcomponents running outside operating system 204 as software stored on computer readable media and executable by hardware and/or firmware, and/or hardware and/or firmware associated with the NIC device itself. As an illustrative example, network interface 212 may be some or all of the following: an agent running within operating system 204 configured to monitor network traffic, an agent running outside of operating system 204 (e.g., in a pre-boot environment) configured to monitor network traffic, and firmware currently installed on the NIC device.

In some embodiments, network interface 212 may be configured to communicate data associated with certain processes 210 running on electronic device 100. For example, network interface 212 may be configured to communicate network feature 226. Network feature 226 may indicate whether a given process 210 has open network ports. In the illustrative example of FIG. 2, network interface 212 may communicate that processes 210A, 210B, 210C, 210E have open network ports, while process 210D does not. As described in more detail below with reference to FIG. 3, such information may be helpful in determining whether certain processes 210 may be classified as malicious or benign and/or in determining to which category of malicious process 210 a process 210 may belong. Although five processes 210 are shown as associated with network interface 212, more or fewer processes 210 may be running at any given time. In some embodiments, only a subset of active processes 210 may be being analyzed, and therefore information regarding only that subset may be collected.

FIG. 3 illustrates a flow chart of an example method 300 for detecting malicious processes running on electronic device 100, in accordance with certain embodiments of the present disclosure. Method 300 includes collecting features for certain processes, classifying the process based on an analysis of those features, and taking action against any identified malicious processes.

According to one embodiment, method 300 preferably begins at step 302. Teachings of the present disclosure may be implemented in a variety of configurations of electronic device 100. As such, the preferred initialization point for method 300 and the order of steps 302-314 comprising method 300 may depend on the implementation chosen.

At step 302, electronic device 100 may identify all processes currently running on electronic device 100. In some configurations, the number of currently running processes may be anywhere from one to thousands. After identifying all currently running processes, method 300 may proceed to step 304.

At step 304, feature collection module 102 of electronic device 100 may collect features describing the selected processes 210. As described in more detail above with reference to FIG. 2, this may include, in some embodiments, gathering data from operating system 204, anti-malware component 206, computer readable media 208, and/or network interface 212. As described below, this may include whether a given process 210 is associated with a start menu or task bar of operating system 204, whether process 210 is hidden or invisible, signed or unsigned, and/or whether process 210 has open network ports. As described in more detail below, more, fewer, or different data may be gathered In some embodiments, collected features may include behavioral as well as structural attributes for the analyzed processes. The collected features may, in some embodiments, be represented as a feature vector comprising a series of binary values representing the presence or absence of certain features. For example, feature collection module 102 may analyze one hundred processes. For each process, feature collection module 102 may collect eight features. Each process may then have an eight bit feature vector. In other examples, more or fewer processes may be analyzed and/or more or fewer features may be collected. As an illustrative example, the collected features may include the following: (A) blacklisted section names, that is a list of section names known to be found in malware ("ContainsBlackListSectionNames"), (B) whether a process has a visible window ("IsWindowInvisible"), (C) whether a process has open network ports ("NetworkUsage"), (D) whether process has an icon in the system tray ("IsInSystemTrayIcon"), (E) whether process has an import table entry for a corresponding API ("IsDebuggerPresent"), (F) whether process image is signed ("IsSigned"), (G) whether process has a shortcut in the start menu ("IsInStartMenuEntry"), and (H) whether the process image is packed ("IsPacked"). In such an illustrative example, where feature collection module 102 has collected these features for a process, a feature vector for this process may look like: <11110011>. Such a feature vector may represent a process that contains blacklisted section names, is invisible, has open network ports, has an icon in the system tray, does not have a debugger present, is not signed, is in the start menu, and is packed. As described in more detail above with reference to FIGS. 1-2, electronic device 100 may collect data from various sources in order to collect these features. After collecting the relevant features from the selected processes, method 300 may then proceed to step 308.

At step 308, method 300 may classify a process as malicious or benign. In some embodiments, feature analysis engine 104 may apply a statistical analysis to the features collected by feature collection module 102 of electronic device 100. Importantly, feature analysis engine 104 may apply the statistical analysis to groups of features at once in order to best determine whether a given process is malicious or benign. In some embodiments, feature analysis engine 104 may be configured to create a set of rules 214, where each rule 214 has an associated weight 216. A rule 214 may be created by applying an inverse dimensionality reduction algorithm to a large set of potentially applicable features in order to create a smaller set of groups of features for analysis. For example, such an algorithm may be applied to a set of test data which may include data samples belonging to a plurality of categories of malicious processes.

In some embodiments, a category of malicious processes may include one or more rules 214, with each rule 214 associated with a weight 216. In some configurations, the weights 216 may be assigned based on experience with classifying categories of malicious processes. In other configurations, a weight 216 may be established through the use of machine learning techniques applied to sample data. In addition to one or more rules 214, a category of malicious processes may have an associated threshold value 218. In some embodiments, a threshold 218 may be assigned based on experience with classifying categories of malicious processes. In other configurations, a threshold 218 may be established through the use of machine learning techniques applied to sample data. As an illustrative example, a support vector machine technique may be used to establish a threshold 218 for a given category.

An illustrative example of the classification algorithm run by feature analysis engine 104 is reproduced in FORMULAS 1-2 below. FORMULA 1 illustrates an example algorithm run by feature analysis engine 104 to calculate a confidence level that a given process belongs to a particular category of malicious process. FORMULA 2 illustrates an example algorithm run by feature analysis engine 104 for classifying a process into a category. FORMULAS 1-2 are illustrated as pseudo-code and should not be read as limiting the configurations to which FORMULAS 1-2 apply. Additionally, FORMULAS 1-2 are provided as illustrative examples only, and other algorithms may be used without departing from the scope of the present disclosure.

---

FORMULA 1 input:     p, where p is the process identification for a given process
The set of rules 214 for category of malicious processes X, $R^X$
Threshold 218 for family X, $T^X$
The weight 216 assigned to a given rule 214 $R_j$ of $R^X$, $w_j$
output:     Confidence for Process p, $C_p$
begin
    k, where k is the number of features in the feature vector;
    $F_p$, where $F_p$ is the feature vector for the process p;
    foreach     Rule, $R_j^X$ where j is a counter of the rules 214 in $R^X$
do
       presence of rule 214 $R_j^X$ in process p, $hit_{p,j}$ =

$$\prod_{m=0}^{k} F_{p,m} \cdot R_{j,m}^X;$$

end $$\text{Weight 216 for process } p, W_p = \sum_{j=0}^{n} w_j \cdot hit_{p,j}$$

Confidence for process p, $C_p = W_p - T^X$;
    return $C_p$;
end

---

As the above pseudo code indicates, the example algorithm may calculate a confidence value for each process under analysis. Such confidence value may be the result of comparing a total weighted threat score for the process to a threshold value 218 for the process category for which the process is being considered for inclusion. As described in more detail below, these process categories may include backdoor, fake alert, and/or downloader malicious processes, as well as benign processes. The total weighted threat score may be calculated by applying a plurality of weights 216 to a statistical analysis of the category rules 214 to the process's feature vector. In some embodiments, each rule 214 for a given process category may have its own weight, as described in more detail below. In some configurations, once the confidence value is determined, the example algorithm of FORMULA 2 may be invoked to determine the process category.

---

FORMULA 2 input :     p, where p is the process identification for a given process
The set of rules 214 for category of malicious processes X, $R^X$
Threshold 218 for family X, $T^X$
Confidence for Process p, $C_p$ -continued

FORMULA 2

```
output :  Category for Process p
begin
        family ← φ ;
        confidence ← 0 ;
        foreach   Category, X   do
                R^X ← rules 214 for family X;
                T^X ← threshold 218 for family X;
                C_p^X = confidence calculated per FORMULA 1;
                if      confidence < C_p^X      then
                        family ← X;
                        confidence ← C_p^X ;
                end
        end
        return family
end
```

Referring again to step 308 of method 300, in some embodiments, a category of malicious processes may have one or more rules 214 used to classify a process into that category. Each rule 214 may have a weight 216 assigned to it. By combining the weighted rules 214, method 300 may classify a process into one or more categories of malicious processes. FORMULAS 1-2 above describe one potential algorithm for accomplishing such a classification. An additional, simplified illustrative example may aid in understanding.

In some configurations, a category of malicious processes may include "backdoor" processes. Generally, a backdoor process may be a process that allows access to certain system resources outside of normal authentication procedures. To test a process for classification as a backdoor process, the following features may be collected: (A) is file hidden, (B) is process window invisible, (C) is process ID hidden, (D) is process running from a temporary memory location, (E) does process contain blacklist section names, (F) is process using network ports, and (G) is process digitally signed. This illustration is simplified and tests may include more, fewer, or different features, depending on the implementation.

Using this illustrative example, TABLE 1 below depicts example data of three example processes running on electronic device 100. The example data uses a value of "1" to denote the presence of a features and a value of "0" to denote the absence of a feature. For example, TABLE 1 shows the example Process 1 as: not hidden (0), invisible (1), having a hidden process ID (1), running from a temporary memory location (1), not containing blacklist section names (0), using network ports (1), and not digitally signed (0). Although seven features and three processes are depicted, more, fewer, or different features and/or processes may be used. Additionally, different systems of denoting the presence and/or absence of certain features may be used. As described in more detail above with reference to step 306, a feature vector for such example data may look like <0111010>. Similarly, the feature vectors for examples processes 2-5 may look like the following: process 2 <1011001>, process 3 <1111111>.

TABLE 1

| | Feature A | Feature B | Feature C | Feature D | Feature E | Feature F | Feature G |
|---|---|---|---|---|---|---|---|
| Process 1 | 0 | 1 | 1 | 1 | 0 | 1 | 0 |
| Process 2 | 1 | 0 | 1 | 1 | 0 | 0 | 1 |
| Process 3 | 1 | 1 | 1 | 1 | 1 | 1 | 1 |

Using these features, the following rules 214 may be applied: (A) is file hidden and is the process window invisible; (B) is the process ID hidden; (C) is process window invisible and is the process running from a temporary memory location; (D) is process window invisible and does the process contain blacklist section names; and (E) is process window invisible, is process using network ports, and is process digitally signed. As this example shows, rules 214 may examine one or more features at one time. This may be because an individual feature, standing alone, may not indicate malicious behavior or may not indicate malicious behavior with a sufficiently high degree of confidence. On the other hand, multiple features, when considered together, may indicate malicious behavior with a sufficiently high degree of confidence.

In some embodiments, this group of rules 214 may be applied to the feature vector to generate a set of threat scores. These threat scores may also have corresponding weights 216. For example, rule 214 (A) may be assigned a weight 216 of 15, rule 214 (B) a weight 216 of 15, rule 214 (C) a weight 216 of 2, rule 214 (D) a weight 216 of 3, and rule 214 (E) a weight 216 of 3. If the total weight 216 of the rules 214' application exceeds a predetermined threshold, this may indicate that the process under consideration is malicious and belongs to the backdoor category. Additionally, the higher above the threshold, the higher the degree of confidence in the classification. A total weighted threat score may be assigned to each process based on the application of the rules 214. Using the example data above, the weighted threat score for example Process 1 may be: [15 (weight 216 assigned to Rule 214 A)*0 (Process 1 does not satisfy Rule 214 A)]+[15 (weight 216 assigned to Rule 214 B)*1 (Process 1 satisfies Rule 214 B)]+[2 (weight 216 assigned to Rule 214 C)*1 (Process 1 satisfied Rule 214 C)]+[3 (weight 216 assigned to Rule 214 D)*1 (Process 1 satisfies Rule 214 D)]+[3 (weight 216 assigned to Rule 214 E)*0 (Process 1 does not satisfy Rule 214 E)]=20.

In some embodiments, this weighted threat score may further be compared against a threshold value 218 associated with each process category. In some embodiments, including the illustrative examples used herein, the weighted threat score must exceed the threshold 218 value. In other embodiments, the weighted threat score may only need to meet or exceed the threshold 218 value. For example, if the threshold 218 for classification as a backdoor process in the current example is 20, then the application of the above-stated weighted rules 214 may determine whether a process is a backdoor process in the following situations, detailed below in TABLE 2.

TABLE 2

| Example | Rule 214 A (15) | Rule 214 B (15) | Rule 214 C (2) | Rule 214 D (3) | Rule 214 E (3) | Total | Backdoor? |
|---|---|---|---|---|---|---|---|
| 1 | 0 | 15 | 2 | 3 | 0 | 20 | No |
| 2 | 0 | 15 | 0 | 0 | 0 | 15 | No |
| 3 | 15 | 15 | 2 | 3 | 3 | 38 | Yes |

As an additional example, in some configurations, a category of malicious processes may include "fake alert" processes. Generally, a fake alert process may be a process that produces inauthentic alerts to the user in order to provoke user action, such as purchasing dangerous products. To test a process for classification as a fake alert process, the following features may be collected: (A) does process not contain white list section names, (B) is process packed, (C) are there malicious words in process memory, (D) is parent of an existing process, (E) is process window invisible, (F) is process in system tray, and (G) is process file hidden. This illustration is simplified and tests may include more, fewer, or different features, depending on the implementation. Of note, certain features may be the same or different as the features used to classify a process into other categories of malicious processes.

Using this illustrative example, TABLE 3 below depicts example data of three example processes running on electronic device 100. For example, TABLE 3 shows the example Process 1 as: not containing white list section names (0), packed (1), having malicious words in process memory (1), being the parent of an existing process (1), not invisible (0), in the system tray (1), and not hidden (0). Although seven features and three processes are depicted, more, fewer, or different features and/or processes may be used. Additionally, different systems of denoting the presence and/or absence of certain features may be used. As described in more detail above with reference to step 306, a feature vector for such example data may look like <0111010>. Similarly, the feature vectors for examples processes 2-3 may look like the following: process 2 <1011001>, process 3 <1111111>.

TABLE 3

|  | Feature A | Feature B | Feature C | Feature D | Feature E | Feature F | Feature G |
|---|---|---|---|---|---|---|---|
| Process 1 | 0 | 1 | 1 | 1 | 0 | 1 | 0 |
| Process 2 | 1 | 0 | 1 | 1 | 0 | 0 | 1 |
| Process 3 | 1 | 0 | 1 | 1 | 1 | 1 | 0 |

Using these features, the following rules 214 may be applied: (A) does process not contain white list section names and is process not packed, (B) does process have malicious words in process memory and is parent nonexistent, (C) is process window invisible and is process in system tray and does process have malicious words in process memory, and (D) is process in system tray and is file hidden. As this example shows, rules 214 may examine one or more features at one time. This may be because an individual feature, standing alone, may not indicate malicious behavior or may not indicate malicious behavior with a sufficiently high degree of confidence. On the other hand, multiple features, when considered together, may indicate malicious behavior with a sufficiently high degree of confidence.

In some embodiments, this group of rules 214 may be applied to the feature vector to generate a set of threat scores. These threat scores may also have corresponding weights 216. For example, rule 214 (A) may be assigned a weight 216 of 10, rule 214 (B) a weight 216 of 5, rule 214 (C) a weight 216 of 15, and rule 214 (D) a weight 216 of 5. If the total weight 216 of the rules 214' application exceeds a predetermined threshold, this may indicate that the process under consideration is malicious and belongs to the backdoor category. Additionally, the higher above the threshold, the higher the degree of confidence in the classification. A total weighted threat score may be assigned to each process based on the application of the rules 214. Using the example data above, the weighted threat score for example Process 1 may be: [10 (weight 216 assigned to Rule 214 A)*0 (Process 1 does not satisfy Rule 214 A)]+[5 (weight 216 assigned to Rule 214 B)*1 (Process 1 satisfies Rule 214 B)]+[15 (weight 216 assigned to Rule 214 C)*0 (Process 1 does not satisfy Rule 214 C)]+[5 (weight 216 assigned to Rule 214 D)*0 (Process 1 does not satisfy Rule 214 D)]=5.

In some embodiments, this weighted threat score may further be compared against a threshold value 218 associated with each process category. For example, if the threshold 218 for classification as a fake alert process in the current example is 20, then the application of the above-stated weighted rules 214 may determine whether a process is a fake alert process in the following situations, detailed below in Table 4.

TABLE 4

| Example | Rule 214 A (10) | Rule 214 B (5) | Rule 214 C (15) | Rule 214 D (5) | Total | Fake alert? |
|---|---|---|---|---|---|---|
| 1 | 0 | 5 | 0 | 0 | 5 | No |
| 2 | 0 | 5 | 0 | 0 | 5 | No |
| 3 | 0 | 5 | 15 | 5 | 25 | Yes |

As an additional example, in some configurations, a category of malicious processes may include "downloader" processes. Generally, a downloader process may be a process that downloads software to an electronic device without the knowledge and/or permission of the user. To test a process for classification as a downloader process, the following features may be collected: (A) does process contain black list section names, (B) is process using network ports, (C) is parent nonexistent, (D) process does not execute from Program Files, (E) file is hidden, and (F) process window is invisible. This illustration is simplified and tests may include more, fewer, or different features, depending on the implementation. Of note, certain features may be the same or different as the features used to classify a process into other categories of malicious processes.

Using this illustrative example, TABLE 5 below depicts example data of three example processes running on electronic device 100. For example, TABLE 5 shows the example Process 1 as: not containing black list section names (0), using network ports (1), having a nonexistent parent (1), not executing from Program Files (1), not hidden (0), and invisible (1). Although six features and three processes are depicted, more, fewer, or different features and/or processes may be used. Additionally, different systems of denoting the presence and/or absence of certain features may be used. As described in more detail above with reference to step 306, a feature vector for such example data may look like <011101>. Similarly, the feature vectors for examples processes 2-3 may look like the following: process 2 <101100>, process 3 <111111>.

TABLE 5

|  | Feature A | Feature B | Feature C | Feature D | Feature E | Feature F |
|---|---|---|---|---|---|---|
| Process 1 | 0 | 1 | 1 | 1 | 0 | 1 |
| Process 2 | 1 | 0 | 1 | 1 | 0 | 0 |
| Process 3 | 1 | 0 | 1 | 1 | 1 | 1 |

Using these features, the following rules 214 may be applied: (A) does process contain black list section names and is using network ports, (B) parent is nonexistent, process does not execute from Program Files, and file is hidden, and (C) parent is nonexistent and process is using network ports and process window is invisible. As this example shows, rules 214 may examine one or more features at one time. This may be because an individual feature, standing alone, may not indicate malicious behavior or may not indicate malicious behavior with a sufficiently high degree of confidence. On the other hand, multiple features, when considered together, may indicate malicious behavior with a sufficiently high degree of confidence.

In some embodiments, this group of rules 214 may be applied to the feature vector to generate a set of threat scores. These threat scores may also have corresponding weights 216. For example, rule 214 (A) may be assigned a weight 216 of 1, rule 214 (B) a weight 216 of 15, and rule 214 (C) a weight 216 of 10. If the total weight 216 of the rules 214' application exceeds a predetermined threshold, this may indicate that the process under consideration is malicious and belongs to the backdoor category. Additionally, the higher above the threshold, the higher the degree of confidence in the classification. A total weighted threat score may be assigned to each process based on the application of the rules 214. Using the example data above, the weighted threat score for example Process 1 may be: [1 (weight 216 assigned to Rule 214 A)*0 (Process 1 does not satisfy Rule 214 A)]+[15 (weight 216 assigned to Rule 214 B)*0 (Process 1 does not Rule 214 B)]+[10 (weight 216 assigned to Rule 214 C)*1 (Process 1 satisfies Rule 214 C)]=10.

In some embodiments, this weighted threat score may further be compared against a threshold value 218 associated with each process category. For example, if the threshold 218 for classification as a downloader process in the current example is 10, then the application of the above-stated weighted rules 214 may determine whether a process is a downloader process in the following situations, detailed below in Table 6.

TABLE 6

| Example | Rule 214 A (1) | Rule 214 B (15) | Rule 214 C (10) | Total | Downloader? |
|---|---|---|---|---|---|
| 1 | 0 | 0 | 10 | 10 | No |
| 2 | 0 | 0 | 0 | 0 | No |
| 3 | 1 | 15 | 10 | 26 | Yes |

As a final example, in some configurations, method 300 may also categorize a process as benign. That is, a process may not be malicious. To test a process for classification as a benign process, the following features may be collected: (A) is process signed, (B) is process in "Add/Remove Programs," (C) is process window visible, and (D) is there no dangling thread. In this illustrative example, "Add/Remove Programs" may be a feature of the Windows operating system that allows a user to add and/or remove new programs. This illustration is simplified and tests may include more, fewer, or different features, depending on the implementation. Of note, certain features may be the same or different as the features used to classify a process into other categories of malicious processes.

Using this illustrative example, TABLE 7 below depicts example data of three example processes running on electronic device 100. For example, TABLE 7 shows the example Process 1 as: not being signed (0), being in Add/Remove Programs (1), being visible (1), and not having a dangling thread (1). Although four features and three processes are depicted, more, fewer, or different features and/or processes may be used. Additionally, different systems of denoting the presence and/or absence of certain features may be used. As described in more detail above with reference to step 306, a feature vector for such example data may look like <0111>. Similarly, the feature vectors for examples processes 2-3 may look like the following: process 2 <1011>, process 3 <1111>.

TABLE 7

| | Feature A | Feature B | Feature C | Feature D |
|---|---|---|---|---|
| Process 1 | 0 | 1 | 1 | 1 |
| Process 2 | 1 | 0 | 1 | 1 |
| Process 3 | 1 | 1 | 1 | 1 |

Using these features, the following rules 214 may be applied: (A) is process signed, (B) is process signed and is process in Add/Remove Programs, (C) is process signed and is process window visible, and is there no dangling thread. As this example shows, rules 214 may examine one or more features at one time. This may be because an individual feature, standing alone, may not indicate malicious behavior or may not indicate malicious behavior with a sufficiently high degree of confidence. On the other hand, multiple features, when considered together, may indicate malicious behavior with a sufficiently high degree of confidence.

In some embodiments, this group of rules 214 may be applied to the feature vector to generate a set of threat scores. These threat scores may also have corresponding weights 216. For example, rule 214 (A) may be assigned a weight 216 of 30, rule 214 (B) a weight 216 of 15, rule 214 and (C) a weight 216 of 15. If the total weight 216 of the rules 214' application exceeds a predetermined threshold, this may indicate that the process under consideration is malicious and belongs to the backdoor category. Additionally, the higher above the threshold, the higher the degree of confidence in the classification. A total weighted threat score may be assigned to each process based on the application of the rules 214. Using the example data above, the weighted threat score for example Process 1 may be: [30 (weight 216 assigned to Rule 214 A)*0 (Process 1 does not satisfy Rule 214 A)]+[15 (weight 216 assigned to Rule 214 B)*0 (Process 1 does not Rule 214 B)]+[15 (weight 216 assigned to Rule 214 C)*0 (Process 1 does not satisfy Rule 214 C)]=0.

In some embodiments, this weighted threat score may further be compared against a threshold value 218 associated with each process category. For example, if the threshold 218 for classification as a benign process in the current example is 30, then the application of the above-stated weighted rules 214 may determine whether a process is a benign process in the following situations, detailed below in Table 8.

TABLE 8

| Example | Rule 214 A (30) | Rule 214 B (15) | Rule 214 C (15) | Total | Benign? |
|---|---|---|---|---|---|
| 1 | 0 | 0 | 0 | 0 | No |
| 2 | 30 | 0 | 15 | 45 | Yes |
| 3 | 30 | 15 | 15 | 60 | Yes |

Referring again to FIG. 3, after classifying the process at step 308, method 300 may proceed to step 310. At step 310, method 300 may determine whether the classification at step 308 identified a suspicious process. In some embodiments, this determination may include determining whether a process was classified into the one or more categories of malicious processes. In other embodiments, this determination may include the above determination, as well as identifying processes identified as having a low level of confidence in the classification. As described above with reference to step 308, the classification process may include a determination of a confidence value. As an illustrative example, the confidence value may be calculated by taking the difference between the weighted total of the rules 214' application to a feature vector and the predetermined threshold 218 for those rules 214. The higher the confidence value, the more likely the process belongs to that category of malicious processes.

In some embodiments, the classification of a process may only proceed if the confidence value is sufficiently high. As an illustrative example, the necessary confidence value may be defined as a percentage of the predetermined threshold. For example, the confidence value may need to be 25% of the threshold value 218 in order to proceed to classification. In other embodiments, the classification of a process may proceed so long as the confidence value is positive. That is, so long as the weighted total of the rules 214' application is higher than the predetermined threshold, the process may be classified into one or more categories of malicious processes. In still other embodiments, a process may be classified so long as the confidence value is non-negative. Such determinations may be highly dependent on the given configuration and may depend, for example, on the tolerances of a given configuration for false positive classifications. In some configurations, one or more of these possibilities may be implemented. That is, a given configuration may identify tiers of potentially malicious processes, including, for example, processes that definitely belong to a particular category (i.e., confidence value >25% threshold 218 value), processes that probably belong to a particular category (i.e., confidence value >threshold 218 value, but confidence value <=25% threshold 218 value), and processes that may belong to a particular category (i.e., confidence value=0).

If, at step 310, method 300 determines that there are suspicious processes, method 300 may proceed to step 312. At step 312, electronic device 100 may take some action against the identified malicious process. Such actions may range from flagging the process for further analysis to placing the process in quarantine, to halting system performance until the user manually determines how to deal with the malicious process. Once an action has been taken, method 300 may proceed to step 314. Additionally, if the process was determined to not be suspicious, method 300 may proceed to step 314.

At step 314, method 300 may determine whether there is another process requiring classification. If such a process exists, method 300 may return to step 308, where that process may undergo the classification procedure. If no such process exists, method 300 may return to step 302, where all running processes may be identified.

Although FIG. 3 discloses a particular number of steps to be taken with respect to method 300, method 300 may be executed with more or fewer steps than those depicted in FIG. 3. In addition, although FIG. 3 discloses a certain order of steps comprising method 300, the steps comprising method 300 may be completed in any suitable order. For example, in the embodiment of method 300 shown, the classification of processes as malicious is shown as sequential, from one process to another. However, in some configurations, it may be necessary or desirable to analyze multiple, if not all, processes simultaneously. Additionally, as described in more detail above with reference to step 310, there may be additional steps included in determining whether and how to identify a process as suspicious. Further, although step 312 shows a single action taking place, multiple actions may be required by multiple parts of electronic device 100 to deal with the identified suspicious process.

Using the methods and systems disclosed herein, certain problems associated with detecting malicious processes in a non-signature based manner may be improved, reduced, or eliminated. For example, the methods and systems disclosed herein allow for detection of malicious processes based on a combination of features that may be based on signatures and/or behaviors.

Although the present disclosure has been described in detail, it should be understood that various changes, substitutions, and alterations can be made hereto without departing from the spirit and the scope of the disclosure as defined by the appended claims.

What is claimed is:

1. At least one non-transitory machine readable storage medium, having instructions stored thereon, the instructions when executed on a machine, cause the machine to:
    collect a plurality of features of each of a plurality of processes;
    apply a plurality of classification rules to the plurality of features, wherein each of the plurality of classification rules corresponds to one or more of a plurality of process categories, and each of the plurality of classification rules comprises a logical combination of a set of the plurality of features;
    apply a plurality of weights to the plurality of classification rules to produce a plurality of weighted threat scores, wherein:
        each weighted threat score corresponds to one or more of the plurality of process categories; and
        at least one of the plurality of weights includes a combination weight applied to a determination of a logical combination of two or more specified features for a particular kind of threat, wherein the combination weight as applied to the logical combination of the two or more specified features is different than a sum of individual weights of the two or more specified features;
    compare the plurality of weighted threat scores to a plurality of threshold values, wherein each of the plurality of threshold values corresponds to one of the plurality of process categories; and
    classify the process in the one or more process categories based at least on the comparison of the plurality of weighted threat scores to the plurality of predetermined thresholds.

2. The medium of claim 1, wherein comparing the plurality of weighted threat scores to a plurality of threshold values comprises assigning a confidence level to each of the plurality of weighted threat scores based at least on the difference between the weighted threat scores and the threshold values.

3. The medium of claim 1, wherein the plurality of process categories comprise a plurality of malicious process categories.

4. The medium of claim 3, wherein the plurality of malicious process categories comprise backdoor malware.

5. The medium of claim 3, wherein the plurality of malicious process categories comprise fake alert malware.

6. The medium of claim 3, wherein the plurality of malicious process categories comprise downloader malware.

7. The medium of claim 1, wherein the plurality of features comprise identifying whether the process is invisible.

8. The medium of claim 1, wherein the plurality of features comprise features indicating a network usage behavior associated with the process.

9. The medium of claim 1, wherein the plurality of features comprise features indicating a system tray behavior associated with the process.

10. The medium of claim 1, wherein the plurality of features comprise features indicating a signed certificate behavior associated with the process.

11. A computerized method for classifying a plurality of processes into a plurality of process categories, the method comprising, for each process of the plurality of processes:
- collecting a plurality of features of each of the plurality of processes with a machine including a processor;
- applying a plurality of classification rules to the plurality of features, wherein each of the plurality of classification rules corresponds to one or more of a plurality of process categories, and each of the plurality of classification rules comprises a logical combination of a set of the plurality of features with the machine;
- applying a plurality of weights to the plurality of classification rules to produce a plurality of weighted threat scores with the machine, wherein:
  - each weighted threat score corresponds to one or more of the plurality of process categories; and
  - at least one of the plurality of weights includes a combination weight applied to a determination of a logical combination of two or more specified features for a particular kind of threat, wherein the combination weight as applied to the logical combination of the two or more specified features is different than a sum of individual weights of the two or more specified features;
- comparing the plurality of weighted threat scores to a plurality of threshold values, wherein each of the plurality of threshold values corresponds to one of the plurality of process categories with the machine; and
- classifying the process in the one or more process categories based at least on the comparison of the plurality of weighted threat scores to the plurality of predetermined thresholds with the machine.

12. The method of claim 11, wherein comparing the plurality of weighted threat scores to a plurality of threshold values comprises assigning a confidence level to each of the plurality of weighted threat scores based at least on the difference between the weighted threat scores and the threshold values.

13. The method of claim 11, wherein the plurality of process categories comprise a plurality of malicious process categories.

14. The method of claim 13, wherein the plurality of malicious process categories comprise backdoor malware.

15. The method of claim 13, wherein the plurality of malicious process categories comprise fake alert malware.

16. The method of claim 13, wherein the plurality of malicious process categories comprise downloader malware.

17. The method of claim 11, wherein the plurality of features comprise features identifying whether the process is invisible.

18. The method of claim 11, wherein the plurality of features comprise features indicating a network usage behavior associated with the process.

19. The method of claim 11, wherein the plurality of features comprise features indicating a system tray behavior associated with the process.

20. The method of claim 11, wherein the plurality of features comprise features indicating a signed certificate behavior associated with the process.

21. The medium of claim 1, further having instructions to cause the machine to uniquely classify the process into one of a plurality of malicious process categories, wherein:
- the malicious process categories each identify a different kind of malicious process; and
- the malicious process categories are included in the one or more process categories.

22. The medium of claim 21, further having instructions to cause the machine to apply a different set of weights according to the classification rules for each malicious process category.

23. At least one non-transitory machine readable storage medium, having instructions stored thereon, the instructions when executed on a machine, cause the machine to:
- collect a plurality of features of each of a plurality of processes;
- apply a plurality of classification rules to the plurality of features, wherein each of the plurality of classification rules corresponds to one or more of a plurality of process categories, and each of the plurality of classification rules comprises a logical combination of a set of the plurality of features;
- apply a plurality of weights to the plurality of classification rules to produce a plurality of weighted threat scores, wherein:
  - each weighted threat score corresponds to one or more of the plurality of process categories, the plurality of process categories including a plurality of malicious process categories including backdoor malware; and
  - at least one of the plurality of weights includes a combination weight applied to a determination of a logical combination of two or more specified features for a particular kind of threat, wherein the combination weight as applied to the logical combination of the two or more specified features is different than a sum of individual weights of the two or more specified features;
- compare the plurality of weighted threat scores to a plurality of threshold values, wherein each of the plurality of threshold values corresponds to one of the plurality of process categories;
- classify the process in the one or more process categories based at least on the comparison of the plurality of weighted threat scores to the plurality of predetermined thresholds; and
- classify the process as backdoor malware based upon applying:
  - a first weight to a determination that both a file of the process is hidden and the process's window is invisible; and
  - a second weight to a determination that a process identifier for the process is hidden.

24. The medium of claim 23, further having instructions to cause the machine to classify the process as backdoor malware based upon applying:
- a third weight to a determination that both the process window is invisible and the process is running from a temporary memory location;
- a fourth weight to a determination both that the process's window is invisible and the process includes blacklisted section names; and
- a fifth weight to a determination that the process's window is invisible, the process is using network ports, and the process is digitally signed.

25. The medium of claim 5, further having instructions to cause the machine to classify the process as fake alert malware based upon applying:
- a first weight to a determination that the process's window is invisible, that the process is in the system tray, and the process has malicious words in process memory.

26. The medium of claim 25, further having instructions to cause the machine to classify the process as fake alert malware based upon applying a second weight to a determination both that the process does not include white list section names and is not packed.

27. The medium of claim 26, further having instructions to cause the machine to classify the process as fake alert malware based upon applying:
   a third weight to a determination both that the process has malicious words in process memory and is parent nonexistent;
   a fourth weight to a determination both that the process is in a system tray and is file hidden.

28. The medium of claim 6, further having instructions to cause the machine to classify the process as downloader malware based upon applying a first weight to a determination that a parent of the process is nonexistent, that the process does not execute from Program Files, and that a file of the process is hidden.

29. The medium of claim 6, further having instructions to cause the machine to classify the process as downloader malware based upon applying a second weight to a determination that a parent of the process is nonexistent, that the process is using network ports, and the process window is invisible.

30. The medium of claim 1, wherein the plurality of features comprises a determination that a given process includes an icon in a system tray, the inclusion of the icon indicating an increased likelihood of malware.

31. A computerized method for classifying a plurality of processes into a plurality of process categories, the method comprising, for each process of the plurality of processes:
   collecting a plurality of features of each of the plurality of processes with a machine including a processor;
   applying a plurality of classification rules to the plurality of features, wherein each of the plurality of classification rules corresponds to one or more of a plurality of process categories, and each of the plurality of classification rules comprises a logical combination of a set of the plurality of features with the machine;
   applying a plurality of weights to the plurality of classification rules to produce a plurality of weighted threat scores with the machine, wherein:
      each weighted threat score corresponds to one or more of the plurality of process categories, the plurality of process categories including a plurality of malicious process categories including backdoor malware; and
      at least one of the plurality of weights includes a combination weight applied to a determination of a logical combination of two or more specified features for a particular kind of threat, wherein the combination weight as applied to the logical combination of the two or more specified features is different than a sum of individual weights of the two or more specified features;
   comparing the plurality of weighted threat scores to a plurality of threshold values, wherein each of the plurality of threshold values corresponds to one of the plurality of process categories with the machine;
   classifying the process in the one or more process categories based at least on the comparison of the plurality of weighted threat scores to the plurality of predetermined thresholds with the machine; and
   classifying the process as backdoor malware based upon applying:
      a first weight to a determination that both a file of the process is hidden and the process's window is invisible; and
      a second weight to a determination that a process identifier for the process is hidden.

* * * * *